United States Patent [19]

Mahe

[11] Patent Number: 6,001,812

[45] Date of Patent: *Dec. 14, 1999

[54] MODULATING BODY/CRANIAL HAIR GROWTH WITH DERIVATIVES OF THE α-TYPE MELANOCYTE-STIMULATING HORMONE

[75] Inventor: Yann Mahe, Morsang sur Orge, France

[73] Assignee: Societe L'Oreal S.A., Paris, France

[ * ] Notice: This patent is subject to a terminal disclaimer.

[21] Appl. No.: 09/012,233

[22] Filed: Jan. 23, 1998

Related U.S. Application Data

[63] Continuation of application No. 08/638,774, Apr. 29, 1996, Pat. No. 5,739,111.

[30] Foreign Application Priority Data

Apr. 28, 1995 [FR] France ................................ 95 05158

[51] Int. Cl.⁶ ........................... A61K 38/00; A61K 38/06
[52] U.S. Cl. ............................................. 514/18; 514/880
[58] Field of Search ............................. 514/18, 881

[56] References Cited

U.S. PATENT DOCUMENTS

| | | | |
|---|---|---|---|
| 4,866,038 | 9/1989 | Hruby et al. | 514/4 |
| 4,879,226 | 11/1989 | Wallace et al. | 435/68 |
| 5,028,592 | 7/1991 | Lipton | 514/8 |
| 5,538,945 | 7/1996 | Pallenberg | 514/6 |

FOREIGN PATENT DOCUMENTS

| | | |
|---|---|---|
| 0293837 | 12/1988 | European Pat. Off. . |
| 88/08695 | 11/1988 | WIPO . |
| 91/07431 | 5/1991 | WIPO . |

OTHER PUBLICATIONS

Patent Abstracts of Japan, vol. 13, No. 515 (C–655) [3863], Nov. 17, 1989, JP–A–01 207225 (Taiyo Kagaku Co).

STN International, Serveur de bases de données, Karlsruhe, DE, fichier Chemical Abstracts, vol. 118, No. 248073.

*Primary Examiner*—Bennett Celsa
*Attorney, Agent, or Firm*—Burns, Doane, Swecker & Mathis, L.L.P.

[57] ABSTRACT

Methods and compositions for inducing or stimulating the growth of body or cranial hair using a peptide which comprises the Lysine-Proline-Valine sequence are described.

11 Claims, No Drawings

MODULATING BODY/CRANIAL HAIR GROWTH WITH DERIVATIVES OF THE α-TYPE MELANOCYTE-STIMULATING HORMONE

This application is a continuation, of Application Ser. No. 08/638,774, filed Apr. 29, 1996 now U.S. Pat. No. 5,739,111.

BACKGROUND OF THE INVENTION

1. Technical Field of the Invention

The present invention relates to the formulation, in a physiologically acceptable medium, of cosmetic/pharmaceutical compositions comprising an effective amount of at least one peptide containing the Lysine-Proline-Valine tripeptide, with the exception of any peptide containing the Lysine-Proline-Valine sequence immediately preceded by an Histidine residue, or of any functional biological equivalent thereof, for promoting or stimulating the growth and/or limiting the loss of body and/or head hair.

2. Description of the Prior Art

In humans, hair growth and its renewal are principally determined by the activity of the hair follicles. Their activity is cyclical and comprises essentially three phases, namely, the anagenic phase, the catagenic phase and the telogenic phase.

The active anagenic phase, or growth phase, which lasts several years and during which the hair grows longer, is followed by a very short and transitory catagentic phase, which lasts a few weeks, and then by a quiescent phase, known as the telogenic phase, which lasts a few months.

At the end of the quiescent period, the hair falls out and another cycle recommences. The head of hair is thus constantly renewed and, of the approximately 150,000 hairs which a head of hair contains, at each instant, approximately 10% of them are at rest and will therefore be replaced in a few months.

In a significant number of cases, early hair loss occurs in subjects who are genetically predisposed thereto and it affects men in particular. It is more particularly androgenetic or androgenic alopecia or, alternatively, androgeno-genetic alopecia.

This alopecia is essentially due to a disturbance in hair renewal which results, at first, in an acceleration in the frequency of the cycles at the expense of the quality of the hair and then of its amount. A progressive thinning of the head of hair takes place by regression of the so-called "terminal" hairs to the downy stage. Regions are preferentially affected, in particular in men the region between the temple and the forehead and, in women, a diffuse alopecia of the vertex is observed.

For many years in the cosmetic or pharmaceutical industry, active agents have been sought for suppressing or reducing the effect of alopecia and, in particular, for inducing or stimulating hair growth or decreasing hair loss.

From this perspective, a large number of highly varied active compounds have already been developed, such as, for example, 2,4-diamino-6-piperidinopyrimidine 3-oxide or "Minoxidil" described in U.S. Pat. No. 4,596,812 or, alternatively, its many derivatives, such as those described, for example, in EP-353,123, EP-356,271, EP-408,442, EP-522,964, EP-420,707, EP-459,890 and EP-519,819.

Also exemplary are 6-amino-1,2-dihydro-1-hydroxy-2-imino-4-piperidinopyrimidine and derivatives thereof, which are more particularly described in U.S. Pat. No. 4,139,619.

It generally remains that it would be advantageous and useful to develop active compounds other than those already known which are potentially more active and/or less toxic, for example compounds which act either on the hair follicle, by promoting its growth, or on the hair cycle, by extending, for example, the anagenic phase, which would have the effect of delaying the change to the quiescent phases and thus of reducing the frequency of the cycles.

SUMMARY OF THE INVENTION

It has now unexpectedly been determined that a peptide containing the Lysine-Proline-Valine tripeptide, or of any functional biological equivalent thereof, with the exception of any peptide containing the Lysine-Proline-Valine sequence immediately preceded by an Histidine residue, efficiently induces and/or stimulates hair growth and/or decreases hair loss.

By "functional biological" equivalent is intended a peptide which is functionally equivalent in terms of biological function, at least one of the amino acid residues of which may have been exchanged for an amino acid residue having a similar hydropathic index.

The hydropathic index is an index attributed to amino acids as a function of their hydrophobicity and of their charge (Kyte et al., *J. Mol. Biol.*, 157, 105 (1982)). This discovery is believed to be the basis of the present invention.

DETAILED DESCRIPTION OF BEST MODE AND SPECIFIC/PREFERRED EMBODIMENTS OF THE INVENTION

More particularly according to the present invention, when employing a peptide containing the Lysine-Proline-Valine tripeptide, it is apparent that the peptide is selected in order to ensure that the amino acids surrounding this tripeptide do not have any effect, either by their nature or by the secondary stucture of the resulting peptide, on the activity for which the peptide is used.

The Lysine-Proline-Valine tripeptide is found, for example, in the peptide sequence of the α-type melanocyte-stimulating hormone (α-MSH) or Melanotropin.

α-MSH was originally described as produced by the pituitary gland but the brain in general, the blood, the skin and other tissues are capable of providing α-MSH activity. It was shown by Schauer et al, *J. Clin. Invest.*, 93, pp. 2258–2262 (May 1994) that the keratinocytes in the epidermis are a source of α-MSH.

α-MSH receptors are present in human scalp follicles (Pigment Cell Res., 4, 193–8, (1991)).

α-MSH (1–13) is known for its antipyretic activity, its anti-inflammatory activity and its propigmentary activity. This neuropeptide is known for inhibiting inflammation induced by cytokines or other mediators of inflammation and by irritants.

The antipyretic signal of α-MSH resides in its carboxy-terminal sequence and can be mimicked by the carboxy-terminal 11–13 (L)Lys(L)Pro(L)Val tripeptide (Watanabe et al, *Brain Research Bulletin*, Vol. 32, pp. 311–314, (1993)). Thus, U.S. Pat. No. 5,028,592 and WO-88/00833 describe the use of the (L or D)Lys-(L)Pro-(L or D)Val tripeptide in an anti-inflammatory treatment and in the preparation of a medicament for treating inflammation.

This invention features the formulation of an effective amount of at least one peptide containing the Lysine-Proline-Valine tripeptide or of any functional biological equivalent thereof, with the exception of any peptide containing the Lysine-Proline-Valine sequence immediately preceded by an Histidine residue, into cosmetic/pharmaceutical compositions intended to induce and/or to stimulate hair growth and/or to retard hair loss.

More particularly, the invention features the use, in cosmetic/pharmaceutical compositions, of an effective amount of the Lysine-Proline-Valine tripeptide to induce and/or to stimulate hair growth and/or to retard or limit hair loss.

Generally, by the term "peptide"n are intended both the "peptide containing the Lysine-Proline-Valine tripeptide, or of any functional biological equivalent, with the exception of any peptide containing the Lysine-Proline-Valine sequence immediately preceded by an Histidine residue" and the isolated "Lysine-Proline-Valine tripeptide". However, in the event that precise terms prove essential, the terms "peptide containing the Lysine-Proline-Valine tripeptide, or of any functional biological equivalent thereof, with the exception of any peptide containing the Lysine-Proline-Valine sequence immediately preceded by an Histidine residue" and "Lysine-Proline-Valine tripeptide" will be used to denote only one or the other embodiment of the invention.

The peptide according to the invention can, of course, be of natural origin. By this is meant that it may have been purified from natural biological material. Exemplary in this respect, α-MSH, which is widely distributed in the central nervous system and which, inter alia, can be purified from the pituitary gland. However, with the advances in chemical engineering, it is now easy to synthesize peptides to measure, even peptides of significant length.

Thus, the present invention features a sufficient amount of the peptide as defined above, said peptide being a peptide of natural or synthetic origin.

In the field of amino acids, the geometry of the molecules is such that they can theoretically exist in the form of different optical isomers. Indeed, the amino acid (aa) has a molecular configuration such that it rotates the plane of polarization of light to the right (dextrorotatory configuration or D-aa) and a molecular configuration such that it rotates the plane of polarization of light to the left (laevorotatory is configuration or L-aa).

Natural amino acids exhibit only the laevorotatory configuration. Consequently, if the peptide used in the compositions according to the invention is of natural origin, it will comprise amino acids of L-aa type. However, chemical synthesis in the laboratory permits the preparation of amino acids having both possible configurations. Starting with this base material, it is possible to incorporate, during the synthesis of peptides, amino acids in the form of both dextrorotatory or laevorotatory optical isomers.

It is thus possible to incorporate, during the synthesis of peptides, Lysine, Proline, Valine amino acid residues without distinction in their D-Lysine (D-Lys), L-Lysine (L-Lys), D-Proline (D-Pro), L-Proline (L-Pro), D-Valine (D-Val) or L-Valine (L-Val) form.

Accordingly, this invention also features the use of a sufficient amount of the peptide as defined above, wherein the amino acid residues of the Lysine-Proline-Valine tripeptide constituting the peptide are without distinction in the form of dextrorotatory or laevorotatory optical isomers.

Exemplary are the peptides containing at least one of the following tripeptides:
D-Lys-D-Pro-D-Val,
D-Lys-D-Pro-L-Val,
D-Lys-L-Pro-D-Val,
D-Lys-L-Pro-L-Val,
L-Lys-D-Pro-D-Val,
D-Lys-L-Pro-L-Val,
L-Lys-D-Pro-L-Val,
L-Lys-L-Pro-D-Val,
L-Lys-L-Pro-L-Val.

According to the invention, more than one peptide can of course be used. In this event, the is mixture of peptides can be composed of one of the possible combinations of the peptides described above.

It may be necessary, for reasons of resistance to degradation, to employ a protected form of the peptide. The nature of the protecting group must obviously be a biologically compatible form. Many. biologically compatible protective groups are suitable, such as, for example, those provided by acylation or acetylation of the amino-terminal end or amidation of the carboxy-terminal end.

Thus, the invention also features the peptide in a protected or unprotected form.

Protective groups based either on acylation or acetylation of the amino-terminal end or on amidation of the carboxy-terminal end or, alternatively, on both, are the preferred.

The effective amount of active principle corresponds to the amount required to attain the desired result.

More particularly, in cosmetic compositions, the peptide is advantageously present in an amount such that the Lysine-Proline-Valine tripeptide is at a concentration ranging from $10^{-12}$ M to $10^{-3}$ M and preferably from $10^{-9}$ M to $10^{-4}$ M.

In medicaments, the peptide is advantageously present in an amount such that the Lysine-Proline-Valine tripeptide is at a concentration ranging from $10^{-12}$ M to 1M and preferably from $10^{-6}$ M to $10^{-1}$ M.

It will be appreciated that one skilled in this art is cognizant that this amount of material is to be adjusted depending on whether the Lysine-Proline-Valine tripeptide is used, or any functional biological equivalent, or the Lysine-Proline-Valine tripeptide, per The pharmaceutical compositions according to the invention can be administered parenterally, enterally or topically. They are preferably administered topically.

In FR-95-01881, assigned to the assignee hereof, an inflammatory stage of alopecia is described. The term alopecia circumscribes a plethora of attacks on the hair follicle having the consequence, whatever the reason, of the partial or general definitive loss of hair. Exemplary thereof are androgenetic alopecia, alopecia areata (pelade) or alopecia totalis, or alternatively alopecia universalis.

Without wishing to be bound by any one theory, it appears that certain alopecias pass through at least one inflammatory stage.

The inflammatory stage of alopecia is characterized, inter alia, by a modification in the level of expression of mediators of inflammation. Exemplary of such mediators are cytokines, including in particular interleukin-1α, interleukin-1β, interleukin-6 or tumour necrosis factors α and β (TNF-α and -β), chemokines, such as interleukin-8 or monocyte chemotactic and activating factor (MCAF), or, alternatively, other chemotactic factors responsible for the recruitment of lymphocyte, monocyte, Langerhans or basophil cells at the inflammatory site, such as leukotrienes $B_4$, or other factors involved in the inflammatory cascade, such as arachidonic acid or prostaglandins, including, in particular, prostaglandins $E_2$.

It has been determined that, in certain subjects, and in particular in those exhibiting a beginning of alopecia, the level of the interleukins is modified. The level of interleukin-1α and of interleukin-8, and more particularly the level of interleukin-1α, is increased in the majority of subjects showing a beginning of alopecia.

It has also been found that, in certain subjects exhibiting an advanced alopecia, the level of prostaglandins $E_2$ is higher than in others, suggesting an involvement of this mediator in the progression of this disorder.

The peptide according to the invention is particularly well suited for retarding hair loss by combating an inflammatory stage of alopecia.

Thus, the present invention also features the formulation of an effective amount of at least one peptide containing the Lysine-Proline-Valine tripeptide, or of any functional biological equivalent thereof, with the exception of any peptide containing the Lysine-Proline-Valine sequence immediatly preceded by an Histidine residue, into cosmetic/pharmaceutical compositions for combating an inflammatory stage of alopecia.

In general, this invention features cosmetic/pharmaceutical compositions comprising an effective amount of at least one peptide containing the Lysine-Proline-Valine tripeptide, or of any functional biological equivalent thereof, with the exception of any peptide just containing the Lysine-Proline-Valine sequence immediately preceded by an Histidine residue, for inducing and/or for stimulating hair growth and/or for slowing or retarding hair loss.

The physiologically acceptable medium in which the peptide is formulated according to the invention can be anhydrous or aqueous. By "anhydrous" medium is intended a solvent medium containing less than 1% of water. This medium can be among a solvent or a mixture of solvents selected, more particularly, from among lower $C_2$–$C_4$ alcohols, such as ethyl alcohol, alkylene glycols, such as propylene glycol, and alkyl ethers of alkylene glycols or of dialkylene glycols, in which the alkyl or alkylene radicals have from 1 to 4 carbon atoms. By "aqueous" medium is intended a medium comprised of water or a mixture of water and another physiologically acceptable solvent, selected, in particular, from among the organic solvents indicated above. In the latter instance, these other solvents, when present, represent approximately 5% to 95% by weight of the composition.

It is possible that the physiologically acceptable medium can contain other adjuvants commonly used in the cosmetics or pharmaceutical field, such as surface-active agents, thickening or gelling agents, cosmetic agents, preservatives or basifying or acidifying agents which are well known to this art, and in amounts which are sufficient to obtain the desired form of presentation, in particular lotions, which are more or less thickened, gels, emulsions or creams. The formulation can optionally be a form pressurized in an aerosol or sprayed from a pump-action spray.

It is also possible to employ, in combination with the peptide, compounds which further improve the activity with respect to hair regrowth and/or with respect to slowing or retarding hair loss and which are known for such activity. Exemplary of these latter compounds are:

(a) nicotinic acid esters, including, in particular, tocopheryl nicotinate, benzyl nicotinate and $C_1$–$C_6$ alkyl nicotinates, such as methyl nicotinate or hexyl nicotinate;

(b) steroidal and nonsteroidal anti-inflammatory agents, in particular hydrocortisone, its salts and its derivatives, niflumic acid, and others;

(c) retinoids, such as all-trans retinoic acid, also known as Tretinoin, Isotretinoin, retinol (or vitamin A), and its derivatives, such as the acetate, the palmitate or the propionate, Motretinide, Etretinate or zinc all-trans retinoate;

(d) pyrimidine derivatives, such as 6-amino-1,2-dihydro-1-hydroxy-2-imino-4-piperidinopyrimidine, also known as Minoxidil, and as described in U.S. Pat. No. 4,139,619;

(e) antibacterial agents, such as macrolides, pyranosides and tetracyclines, and in particular Erythromycin;

(f) calcium antagonist agents, such as Cinnarizine and Diltiazem;

(g) hormones, such as estriol or analogs, or thyroxine and its salts;

(h) antiandrogen agents, such as oxendolone, spironolactone or diethylstilbestrol;

(i) 5α-reductase inhibitors;

(j) OH-radical scavengers, such as dimethyl sulphoxide.

Other compounds can also be added, for example, Diazoxide, Spiroxazone, phospholipids, such as lecithin, linoleic and linolenic acids, salicylic acid and its derivatives described in FR-2,581,542, such as the derivatives of salicylic acid bearing an alkanoyl group having from 2 to 12 carbon atoms in the 5 position of the benzene ring, hydroxycarboxylic or ketocarboxylic acids and their esters, lactones and their corresponding salts, Anthralin, carotenoids, eicosatetraenoic and eicosatrienoic acids and their esters and amides, or vitamin D and its derivatives.

The cosmetic compositions according to the invention are applied to the alopecic regions of the scalp and of the hair of a human individual, and is optionally maintained in contact for a number of hours, and is optionally rinsed therefrom. It is possible, for example, to apply a composition containing an effective amount of the peptide to the hair and the scalp in the evening, to maintain the composition in contact overnight and optionally to shampoo in the morning. These applications can be repeated daily for one or a number of months, depending on the particular individuals.

Thus, the present invention also features a regimen for the cosmetic treatment of the hair and/or of the scalp, comprising topically applying to the hair and/or the scalp a composition containing an effective amount of at least one peptide which comprises the Lysine-Proline-Valine tripeptide, permitting said composition to remain in contact with the hair and/or the scalp, and, optionally, rinsing same therefrom.

This treatment exhibits the characteristics of a cosmetic regime insofar as it improves the attractiveness of the hair by providing it with greater liveliness and an enhanced appearance.

In order to further illustrate the present invention and the advantages thereof, the following specific examples are given, it being understood that same are intended only as illustrative and in nowise limitative.

In said examples to follow, Ac-LPV-NH$_2$ denotes Acetyl-Lys-Pro-Val-NH$_2$.

EXAMPLE 1

Measurement of the Effect of the Ac-LPV-NE$_2$ Tripeptide and of the α-type Melanocyte-stimulating Hormone (α-MSH) on the Lengthening and the Survival of Hair Follicles Maintained in Vitro:

Viable in vitro hair follicles were prepared according to the technique described in French Patent Application No. 95–08465, filed Jul. 12, 1995 and assigned to the assignee hereof.

From a scalp biopsy, a rather fine strip of scalp was isolated using a scalpel. The adipose tissue surrounding the follicles was removed with microforceps while avoiding damage to the hair bulb. The follicles were cut out with a scalpel under a microscope in order to separate them from their epidermal and dermal surroundings.

The follicles were then cultured in the wells of Costar-type 24-well plates, at the rate of one follicle per well. Each well contained 0.5 ml of Williams' medium E, to which had been added penicillin and streptomycin to a final concentration of 50 IU/ml, glutamine to 2 mM, bovine insulin to 0.01 mg/ml and hydrocortisone to 0.04 mg/ml.

The follicles were then measured using a microscope equipped with a micrometric eyepiece.

After 24 hours, the follicles were again measured and those which had lengthened by less than 0.3 divisions of the micrometer, corresponding to 0.16 mm, were discarded.

The follicles retained for the experimentation was then cultured in Williams' medium E containing or not containing the Ac-LPV-NH$_2$ tripeptide or α-MSH.

The five (5) following culturing conditions were tested:
Condition A: Complete Williams' medium E, without peptide.
Condition B: Complete Williams' medium E+10 mM Ac-LPV-NH$_2$.
Condition C: Complete Williams' medium E+1 mM Ac-LPV-NH$_2$.
Condition D: Complete Williams' medium E+0.1 mM Ac-LPV-NH$_2$.
Condition E: Complete Williams' medium E+1 mM α-MSH.

| Days | Mean lengthening | Standard deviation | n | % Survival |
|---|---|---|---|---|
| Condition A: | | | | |
| 0 | 0.00 | 0.00 | 12 | 100 |
| 1 | 0.36 | 0.04 | 12 | 100 |
| 4 | 0.91 | 0.14 | 12 | 100 |
| 5 | 1.03 | 0.17 | 11 | 92 |
| 6 | 1.10 | 0.20 | 7 | 58 |
| 7 | 1.18 | 0.22 | 6 | 50 |
| 8 | 1.32 | 0.19 | 5 | 42 |
| 11 | 1.71 | 0.13 | 2 | 17 |
| 12 | 1.79 | 0.16 | 2 | 17 |
| Condition B: | | | | |
| 0 | 0.00 | 0.00 | 12 | 100 |
| 1 | 0.38 | 0.06 | 12 | 100 |
| 4 | 1.11 | 0.15 | 12 | 100 |
| 5 | 1.33 | 0.18 | 12 | 100 |
| 6 | 1.43 | 0.20 | 12 | 100 |
| 7 | 1.54 | 0.24 | 12 | 100 |
| 8 | 1.74 | 0.27 | 11 | 92 |
| 11 | 1.96 | 0.41 | 10 | 83 |
| 12 | 2.40 | 0.40 | 5 | 42 |
| Condition C: | | | | |
| 0 | 0.00 | 0.00 | 11 | 100 |
| 1 | 0.38 | 0.08 | 11 | 100 |
| 4 | 1.05 | 0.22 | 11 | 100 |
| 5 | 1.21 | 0.26 | 11 | 100 |
| 6 | 1.28 | 0.30 | 11 | 100 |
| 7 | 1.42 | 0.27 | 10 | 91 |
| 8 | 1.39 | 0.26 | 6 | 55 |
| 11 | 1.70 | 0.46 | 4 | 36 |
| Condition D: | | | | |
| 0 | 0.00 | 0.00 | 12 | 100 |
| 1 | 0.37 | 0.05 | 12 | 100 |
| 4 | 1.10 | 0.14 | 12 | 100 |
| 5 | 1.22 | 0.17 | 12 | 100 |
| 6 | 1.28 | 0.18 | 12 | 100 |
| 7 | 1.42 | 0.22 | 10 | 83 |
| 8 | 1.58 | 0.28 | 6 | 50 |
| 11 | 2.08 | 0.26 | 5 | 42 |
| 12 | 2.11 | 0.00 | 2 | 17 |
| Condition E: | | | | |
| 0 | 0.00 | 0.00 | 11 | 100 |
| 1 | 0.37 | 0.07 | 11 | 100 |
| 4 | 1.20 | 0.17 | 11 | 100 |
| 5 | 1.26 | 0.18 | 11 | 100 |
| 6 | 1.44 | 0.18 | 10 | 91 |
| 7 | 1.58 | 0.17 | 9 | 82 |
| 8 | 2.07 | 0.17 | 5 | 45 |
| 11 | 2.26 | 0.21 | 4 | 36 |

These results evidenced that the Ac-LPV-NH$_2$ tripeptide and α-MSH promoted the lengthening of the cultured hair follicles and increased their survival time. The increase in the survival time corresponds to a lengthening of the phase of the cycle in which the hair is present and thus promotes delaying the loss thereof.

EXAMPLE 2

Examples of Compsitions Comprising a Peptide According to the Invention:

These compositions were formulated via the usual techniques conventionally employed in cosmetics or in pharmacology.

Liposomed gel:

| | |
|---|---|
| Natipide II[1] (i.e. 2 g of phospholipids) | 10 g |
| Ac-LPV-NH$_2$ | $5 \cdot 10^{-5}$ g |
| Carbomer | 0.25 g |
| Triethanolamine | q.s. pH = 7 |
| Preservatives | q.s. |
| Demineralized water q.s. for 100 g | |

[1]water/alcohol/lecithin mixture marketed by Nattertmann

Niosomed gel:

| | |
|---|---|
| Chimexane NS[1] | 1.8 g |
| Monosodium stearoylglutamate | 0.2 g |
| Ac-LPV-NH$_2$ | $7.5 \cdot 10^{-4}$ g |
| Carbomer | 0.2 g |
| Triethanolamine | q.s. pH = 7 |
| Preservatives | q.s. |
| Fragrances | q.s. |
| Demineralized water q.s. for 100 g | |

[1]Non-ionic surfactant marketed by Chimex.

Niosomed lotion:

| | |
|---|---|
| Chimexane NL[1] | 0.475 g |
| Cholesterol | 0.475 g |
| Monosodium stearoylglutamate | 0.05 g |
| Ac-LPV-NH$_2$ | $10^{-3}$ g |
| Preservatives | q.s. |
| Dyes | q.s. |
| Fragrance | q.s. |
| Demineralized water q.s. for 100 g | |

[1]Non-ionic surfactant marketed by Chimex.

Spray:

| | |
|---|---|
| Ac-LPV-NH$_2$ | $5 \cdot 10^{-6}$ g |
| Minoxidil | 0.5 g |
| 95° Ethanol | 55.1 g |
| Propylene glycol | 22.8 g |
| Fragrance | q.s. |
| Demineralized water q.s. for 100 g | |

Care cream: O/W emulsion

| | |
|---|---|
| Cetostearyl alcohol/Cetostearyl alcohol | 5 g |

-continued

| | |
|---|---|
| oxyethylenated with 33 mol of ethylene oxide (80/20) | |
| Glyceryl monostearate | 1.5 g |
| Cetyl alcohol | 0.75 g |
| Liquid petrolatum | 10 g |
| Polydimethylsiloxane | 0.75 g |
| Glycerol | 4 g |
| Preservatives | q.s. |
| Ac-LPV-NH$_2$ | $5 \cdot 10^{-3}$ g |
| Demineralized water q.s. for 100 g | |
| Daily lotion: | |
| Ac-LPV-NH$_2$ | $12.5 \cdot 10^{-6}$ g |
| Diaminopyrimidine 3-oxide | 0.75 g |
| 95° Ethanol | 30 g |
| Fragrance | q.s. |
| Dyes | q.s. |
| Demineralized water q.s. for 100 g | |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for inducing or stimulating the growth of body or head or cranial hair or retarding or limiting the loss of such hair on a mammalian organism in need of such treatment, comprising administering to such organism a therapeutically effective amount of a composition comprising at least one peptide containing a Lysine-Proline-Valine tripeptide, with the exception of any peptide containing the Lysine-Proline-Valine sequence immediately preceded by a histidine residue and with the further exception of any peptide containing the Lysine-Proline-Valine sequence which is complexed to a metal.

2. The method as defined by claim 1, said at least one peptide being the Lysine-Proline-Valine tripeptide.

3. The method as defined by claim 1, said at least one peptide comprising a peptide of natural or synthetic origin.

4. The method as defined by claim 1, the amino acid residues of the Lysine-Proline-Valine tripeptide comprising the tripeptide being in the form of dextrorotatory or laevorotatory optical isomers.

5. The method as defined by claim 1, said at least one peptide comprising protective groups therefor.

6. The method as defined by claim 5, said protective groups being provided by acylation or acetylation of the amino-terminal end or by amidation of the carboxy-terminal end, or by both.

7. The method as defined by claim 1, comprising treating an inflammatory stage of alopecia.

8. The method as defined by claim 1, said Lysine-Proline-Valine tripeptide being administered at a concentration of from $10^{-12}$ M to $10^{-3}$ M.

9. The method as defined by claim 1, said Lysine-Proline-Valine tripeptide being administered at a concentration of from $10^{-12}$ M to 1 M.

10. The method as defined by claim 1, comprising topically applying said at least one peptide to human hair and/or a human scalp.

11. The method as defined by claim 10, comprising maintaining said at least one peptide in contact with said hair/scalp for such period of time as is required to elicit the desired therapeutic response, and optionally rinsing same therefrom.

* * * * *